(12) United States Patent
Figley et al.

(10) Patent No.: US 7,255,105 B2
(45) Date of Patent: Aug. 14, 2007

(54) SYSTEM FOR USE IN ADMINISTRATING THERAPEUTIC GAS TO A PATIENT

(75) Inventors: Curlis Figley, Edmonton (CA); Darin W Hunt, Edmonton (CA)

(73) Assignee: Pulmonox Technologies Corporation, Edmonton, Alberta (CA)

( * ) Notice: Subject to any disclaimer, the term of this patent is extended or adjusted under 35 U.S.C. 154(b) by 683 days.

(21) Appl. No.: 10/351,755

(22) Filed: Jan. 27, 2003

(65) Prior Publication Data

US 2003/0131849 A1    Jul. 17, 2003

Related U.S. Application Data

(63) Continuation-in-part of application No. 09/688,229, filed on Oct. 16, 2000, now Pat. No. 6,668,828.

(51) Int. Cl.
   *A62B 9/02* (2006.01)

(52) U.S. Cl. ............... 128/205.24; 128/203.11; 128/204.18

(58) Field of Classification Search ........... 128/203.11, 128/204.18, 205.24
See application file for complete search history.

(56) References Cited

U.S. PATENT DOCUMENTS

| | | | | |
|---|---|---|---|---|
| 5,551,391 | A * | 9/1996 | Beck et al. | 123/305 |
| 6,439,305 | B1 * | 8/2002 | Bakke | 166/242.6 |
| 6,672,328 | B2 * | 1/2004 | Colussi et al. | 137/102 |
| 6,688,578 | B1 * | 2/2004 | Nussio et al. | 251/129.15 |

* cited by examiner

*Primary Examiner*—Michael J. Hayes
*Assistant Examiner*—Michael G. Mendoza
(74) *Attorney, Agent, or Firm*—Terry M Gernstein

(57) ABSTRACT

A system controls and manages administration of a therapeutic gas, such as NO, $O_2$, or the like, to a patient. The system includes an equalizing valve and a reservoir.

7 Claims, 13 Drawing Sheets

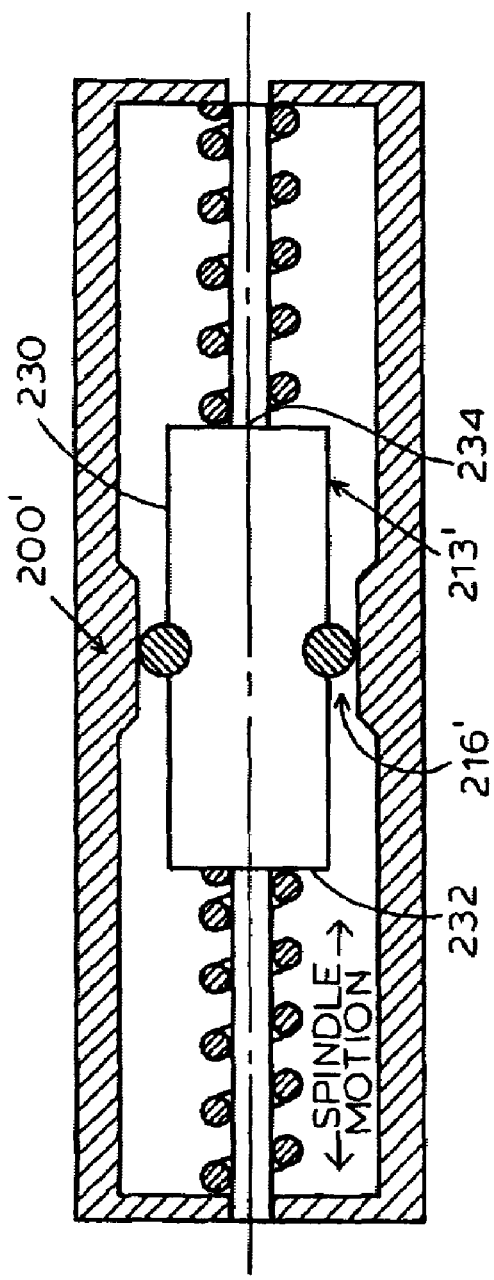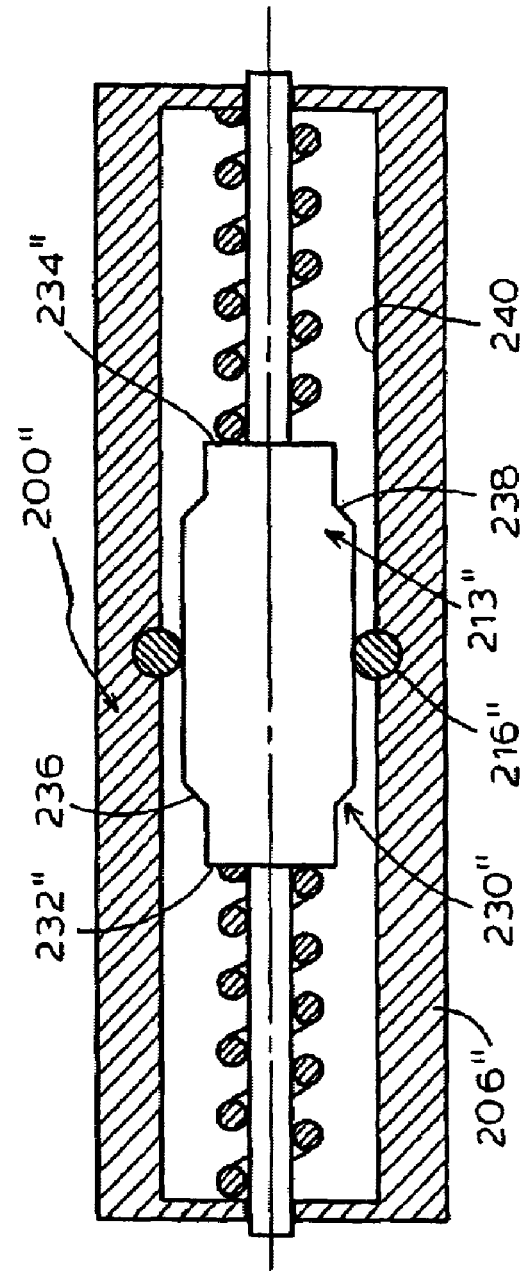

SYSTEM FOR USE IN ADMINISTRATING THERAPEUTIC GAS TO A PATIENT

CROSS REFERENCE TO RELATED APPLICATIONS

The present application is a continuation-in-part application Ser. No. 09/688,229 filed on Oct. 16, 2000 now U.S. Pat. No. 6,668,828 and owned by the same assignee. The present application incorporates herein the disclosure of the Ser. No. 09/688,229 patent application by reference.

TECHNICAL FIELD OF THE INVENTION

The present invention relates to the general art of surgery, and to the particular field of introducing material to a patient for therapeutic or diagnostic purposes, most specifically, the invention relates to NO therapy.

BACKGROUND OF THE INVENTION

As discussed in the referenced and incorporated disclosure, the use of therapeutic gases to treat a human or animal patient has been known in the art for many years. A number of different gases may be added to a respiratory gas that is inhaled by a patient. It is noted that this application merely refers to a "patient" because it is intended to encompass within its scope the is following situations: a spontaneously breathing, non-ventilated patient, as well as a spontaneously breathing, mechanically-ventilated patient, as well as a non-spontaneously breathing, mechanically-ventilated patient. Accordingly, the term "patient" is intended to cover all of these situations and/or combinations thereof. These gases may be used to achieve some therapeutic effect, service a diagnostic function or have some other desirable purpose. Such gases will be referred to herein as therapeutic gases. One skilled in the delivery of therapeutic gas will understand that the disclosure can be used to teach either human or animal patients. Accordingly, no limitation to human is intended by references to patient in this disclosure.

One therapeutic gas is nitric oxide (NO), which is administered by inhalation in low concentrations to treat primary or secondary pulmonary hypertension or other diseases. In many cases, nitric oxide or other therapeutic gases come from a high concentration source such as a high concentration compressed gas cylinder. The gas source may be pure or may contain some concentration of therapeutic gas in a carrier gas. There may also be cases where more than one therapeutic gas is used, with or without a carrier gas or gases. It is often necessary to dilute therapeutic gas to a lower concentration and mix it with air and/or oxygen prior to delivery to the patient. This dilution may be necessary to achieve a desired dosage concentration and/or to avoid or reduce adverse bioeffects that may occur if high concentration gas is delivered to the patient. If the therapeutic/carrier gas is not sufficiently oxygenated, it is necessary to mix it with air prior to delivery to the patient. In some cases, it is necessary to add supplemental oxygen to the mixture to avoid a hypoxic respiratory mixture or to enrich the oxygen content of the respiratory gas above twenty-one percent. In the latter case, the oxygen will also be considered as a therapeutic gas.

NO is one of a number of therapeutic gases that are administered to a patient and require dilution from a high concentration form to a lower, safer concentration before administration to a patient. NO will be the primary focus of this disclosure; however, one skilled in the surgical arts will understand that the disclosure can be used to teach other gases as well. Accordingly, no limitation to NO is intended by the references to NO in this description.

The art contains several devices and systems to deliver therapeutic gas to a patient.

The referenced disclosure discusses several systems for administering therapeutic gas to a patient.

Many systems that are used to administer therapeutic gas to a patient include primary gas sources in the form of pressurized cylinders. Some of these systems include a flow direction check valve downstream of the inlet to seal the downstream portions of the system when the supply pressure is removed. However, a check valve isolation system may have drawbacks if used in certain circumstances.

When a pressurized gas source is exchanged, there exists the possibility that air will be trapped within the inlet volume of the system plumbing that is exposed to air during the source exchange. Specifically, in a check valve system, this volume includes the volume upstream of the sealing mechanism of the check valve. It is desirable to keep that exposed volume of plumbing as small as possible so the resulting trapped air volume is reduced. Any trapped air will normally degrade the quality of the high purity gases contained within the remainder of the system when intervening valves are opened. This degradation is proportional to the volume of trapped air.

Therefore, it is desirable to maintain this dead volume to a minimum. Note that the concept of dead volume should also be read to include dead surface area within the scope of this discussion. The trapped air volume will also be referred to as the dead volume in this disclosure. Surface area plays an important role in gas plumbing quality since contaminants often preferentially adhere to surfaces and can be extremely difficult to remove.

Furthermore, it is advantageous to provide a system sealing action as close to the supply inlet as possible to further minimize the dead space volume upstream of the sealing surfaces.

Typically, a flow direction check valve is not able to achieve all of these goals.

It is noted that it is possible to flush or purge the system to remove contaminated gas from dead space regions. However, for purging to be effective, the dead space must be substantially swept out and internal surfaces scrubbed by periods of high gas flow. If there are poorly swept regions within the dead space, purging will have to be extended to allow for diffusion and other gas exchange mechanisms to remove or dilute the contamination. Therefore, there is a need for a means for ensuring proper purging of a system used to administer therapeutic gas to a patient.

Furthermore, purging requirements are strongly dependent on the relative size and geometry of the contaminated volumes and surfaces. Purging is often complicated in many situations due to possible toxic effects of the therapeutic gases on bystanders and the high cost of medical grade gases.

The incorporated disclosure notes that there is a further need for a valve that will make purging most efficient and effective.

Furthermore, the referenced disclosure notes that an autonomous gas delivery system should be able to detect the supply pressure so when a pressurized cylinder has been attached and the supply valve opened, a control system is signaled.

The referenced disclosure further notes that in order to maintain low inlet dead space, a supply pressure sensor must be located on the downstream side of an inlet sealing mechanism. In the prior art, a simple back flow prevention check valve has provided this function. A check valve will seal when there is a lower supply pressure on the upstream side of the check valve than in the downstream plumbing (thus checking the backward flow of gas). If the check valve seals, the pressure sensor, which is located further downstream in the system than the check valve, will continue to show the last supply pressure when the check valve closes. The pressure sensor may not indicate the actual supply pressure, which typically drops to atmospheric pressure when the supply is disconnected. If, subsequent to this, a supply is attached that is at a lower pressure than the checked pressure, the system will not be able to detect the connection until the pressure downstream of the check valve has been bled off as well as not at all.

Accordingly, as discussed in the referenced disclosure, there is a need for a means for sealing a system such as disclosed herein which will be able to fully detect pressure and control the flow of the system during changing of gas sources.

The referenced disclosure observes that in general, it is desirable to close off the inlet of a system such as disclosed herein when a supply is detached and to maintain the inside of the high purity system at a slight positive pressure with respect to atmospheric pressure.

The advantages of this isolated input but slight remaining positive pressure situation include: the chance of contamination is reduced; minor leaks that may be present will tend to leak in an outward fashion; the limited maximum internal to inlet side pressure allows the downstream pressure sensor to detect a disconnection of a supply with any significant pressure; and allows the system to detect the connection of another supply with a pressure significantly above atmospheric.

As discussed in the referenced disclosure, there is a need for a means for connecting the system of the present invention to a source of gas that will reduce the possibility of contamination of the system. Therefore, there is a need for a mechanism that can minimize dead space volume.

The referenced disclosure discusses an equalizing valve that simultaneously satisfies a number of objectives and overcomes many problems associated with prior therapeutic gas delivery systems.

Still further, there are situations in which the main supply source for a system must be removed from the system. For example, the main source must often be removed to be replaced with an alternate source. Replacement may be required if: the primary source is depleted; if a portable gas source is being replaced by a stationary source (or vise versa); or if the gas source is being exchanged for an alternate therapeutic gas composition. Other situations that may require the removal of the gas source include but are not limited to preparation for temporary storage or shipment, periodic maintenance and transport between use locations.

As discussed in the referenced disclosure, contamination of the therapeutic gases, such as mixing therein atmospheric gases, is undesirable.

In many therapeutic gas delivery situations, gas delivery to the patient must be temporarily disrupted in order to change supply source, or the like. Such disruption is undesirable. In order to obviate such disruption, some gas delivery systems include either a second large source or an external back-up source of therapeutic gas. Either of these solutions can be costly and cumbersome.

Still further, if, for some reason, the primary gas source ceases supplying gas to the system and an operator does not immediately replace the gas source, delivery of gas to the patient may be interrupted, or even contaminated. Neither of these situations is desirable.

Therefore, there is a need for a therapeutic gas delivery system in which continuous gas delivery to a patient is ensured, even if the main gas source ceases delivering gas for a short period of time.

OBJECTS OF THE INVENTION

It is a main object of the present invention to provide a system and elements for delivering NO to a spontaneously breathing, and/or a non-spontaneously breathing and or a mechanically ventilated patient or a non-ventilated patient.

It is another object of the present invention to provide a system and elements for delivering NO to a patient that is compatible with periodic, routine or continuous modes of operation.

It is another object of the present invention to provide a system and elements for delivering NO to a spontaneously breathing, mechanically-ventilated patient that is easily used by patients, clinical staff and other caregivers with a wide and varying range of skills.

It is another object of the present invention to provide a system and elements for delivering NO to a patient that is easily cleaned, purged and maintained.

It is another object of the present invention to provide a system and elements for delivering NO to a patient that is easily monitored.

It is another object of the present invention to provide a system and elements for delivering NO to a patient that has any limited lifetime elements thereof easily replaced.

It is another object of the present invention to provide a system and elements for delivering NO to a patient which can deliver any desired therapeutic gas or combination of gases to the patient in an efficient and effective manner.

It is another object of the present invention to provide a system and elements for delivering NO to a patient which has alarms and alarm systems.

It is another object of the present invention to provide a system and elements for delivering NO to a patient which is adaptable to a wide variety of conditions and system requirements.

It is another object of the present invention to provide a system and elements for delivering NO to a patient which has means for delivering desired therapeutic gases even while a main source of gas is being replaced.

It is another object of the present invention to provide a system and elements for delivering NO to a patient which is portable.

It is another object of the present invention to provide a system and elements for delivering NO to a patient which is autonomous.

It is another object of the present invention to provide a system and elements for delivering NO to a patient which has a means for effectively and efficiently equalizing pressure between a source of pressurized gas and the system, but keeping the system pressurized slightly above atmospheric pressure if the gas source is removed.

It is another object of the present invention to provide a system and elements for delivering NO to a patient that maintains dead volume to a minimum.

It is another object of the present invention to provide a system and elements for delivering NO to a patient that includes an equalizing valve that can minimize dead space volume.

It is another object of the present invention to provide a system and elements for delivering NO to a patient that includes a means for ensuring is proper purging of a system used to administer therapeutic gas to the patient.

It is another object of the present invention to provide a system and elements for delivering NO to a patient that includes a valve that will make purging most efficient and effective while overcoming the problems associated with the prior art.

It is another object of the present invention to provide a system and elements for delivering NO to a patient that includes a means for sealing a system such as disclosed herein which will be able to fully detect pressure and control the flow of the system during changing of gas sources.

It is another object of the present invention to provide a system and elements for delivering NO to a patient that includes a means for connecting the system to a source of gas that will reduce the possibility of contamination of the system.

It is another object of the present invention to provide a therapeutic gas delivery system where continuous gas delivery to a patient is maintained, even if the main gas source ceases delivering gas for a short period of time. This main gas supply disruption period includes when inlet purging is occurring after the main gas source connection is restored.

SUMMARY OF THE INVENTION

These, and other, objects are achieved by a system that administers therapeutic gas to a patient which incorporates all of the teaching of the referenced and incorporated disclosure and which includes one or more equalizing valves fluidically connecting a source of therapeutic gas to the system. A reservoir is included in the system to ensure continuous supply of therapeutic gas to the patient even if the main source of therapeutic gas is temporarily interrupted.

The equalizing valve of the present invention satisfies the above-stated objects. The valve is positioned directly at the inlet of the devices gas system by being incorporated into the supply connection fitting. The equalizing valves sealing surfaces within the fitting is located close to the tip of the connection fitting. The remaining upstream volume of the connection fitting is reduced by substantially filling that volume with a pin, leaving only a thin annulus for gas to pass into the system. This geometry helps preserve the downstream gas purity and will significantly reduce the required amount of gas for each purge cycle. The equalizing valve also permits proper supply pressure detection and subsequent purging of the system when necessary as discussed previously.

The equalizing valve operates to pass flow in either direction as long as a minimum value of differential pressure exists across it. When this minimum differential pressure is not met, the equalizing valve seals and prevents flow in either direction. This provides for a dead band in the flow action through the valve.

The equalizing valve of the present invention also permits easy use of several sources of therapeutic gas. Thus, for example, a portable source can be easily changed over to a bedside source, or several small sources can be used in place of a single large source. Changing of source gas is made easy because the equalization valve keeps the system clean.

The valve of the present invention maintains a sufficient positive internal pressure to ensure that air does not migrate into the high purity gas regions while a source gas is disconnected. Furthermore, gas is not allowed to enter the reservoir and the source is not connected to the patient until a sufficiently high supply pressure is attached to the system, the pressure is detected and a purge cycle is completed. As an added safety feature, the valve of the present invention automatically throttles itself in the event of a massive downstream leak.

The reservoir of the present invention maintains a volume of gas available for delivery to the patient even if delivery of gas from the main source is discontinued for a period of time. The reservoir is also designed so that incoming gas is required to flow therethrough so that during active delivery the gas residency time in the reservoir is reduced. Thus, the possibility of stagnation of therapeutic gas in the reservoir is, if not obviated, at least reduced.

The reservoir can be formed of a single container or plural containers, with the advantages associated with either or both forms being realizable with the system embodying the present invention.

BRIEF DESCRIPTION OF THE DRAWING FIGURES

Figure 2:
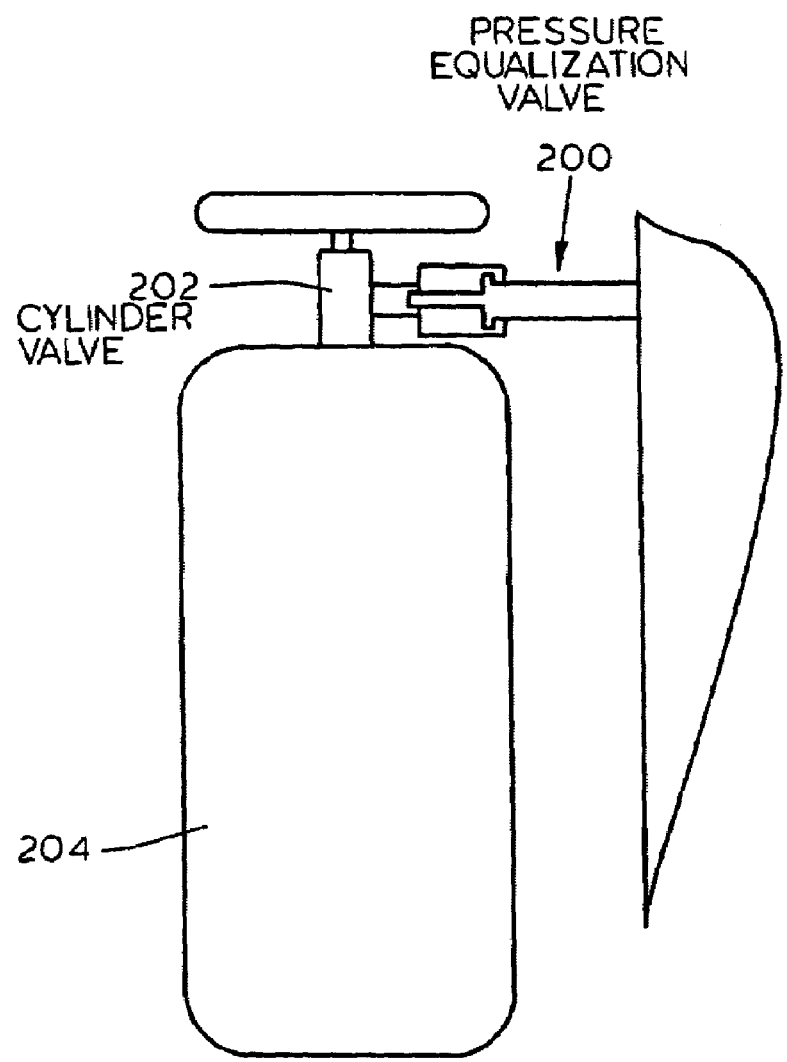
FIG. 2 is a pressure equalization valve in conjunction with a source of gas as used in conjunction with a system embodying the present invention and corresponds to FIG. 15 of the referenced disclosure.
Figure 3:
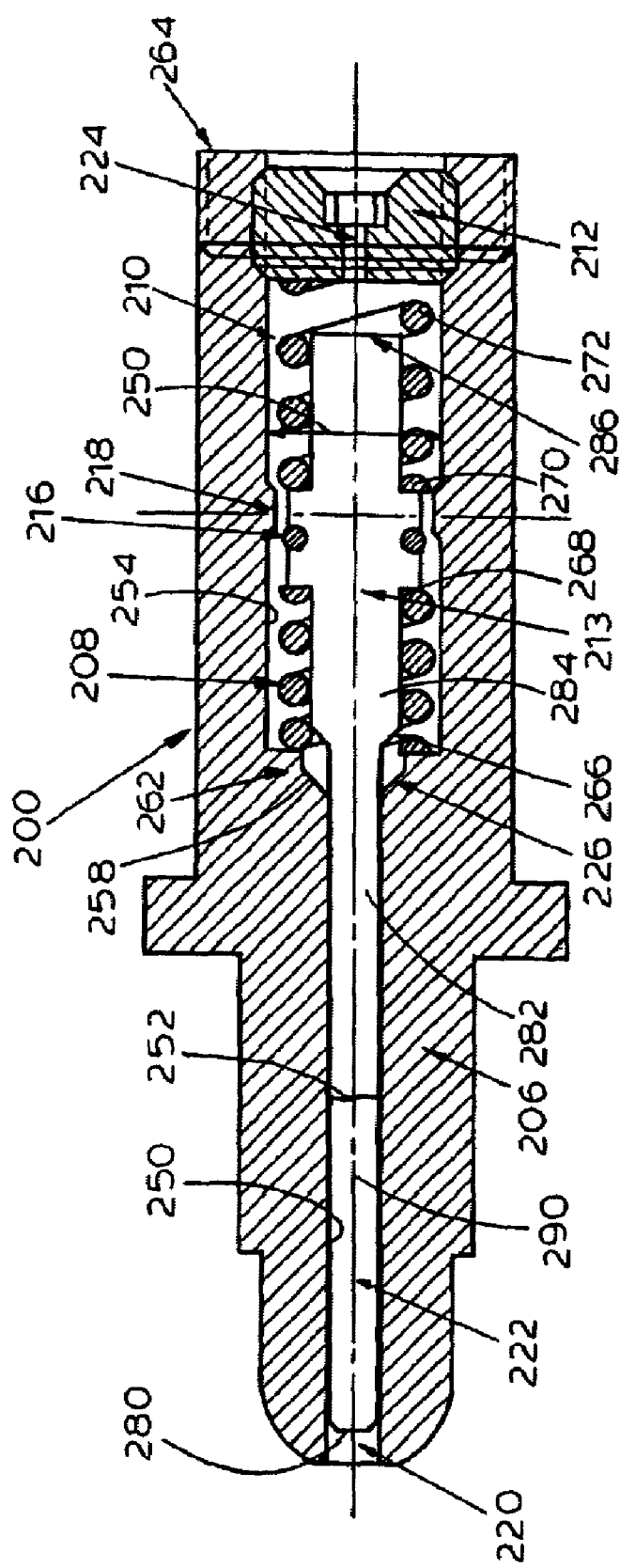
FIG. 3 shows the pressure equalization valve of FIG. 2 in a first condition and corresponds to FIG. 16 of the referenced disclosure.
Figure 4:
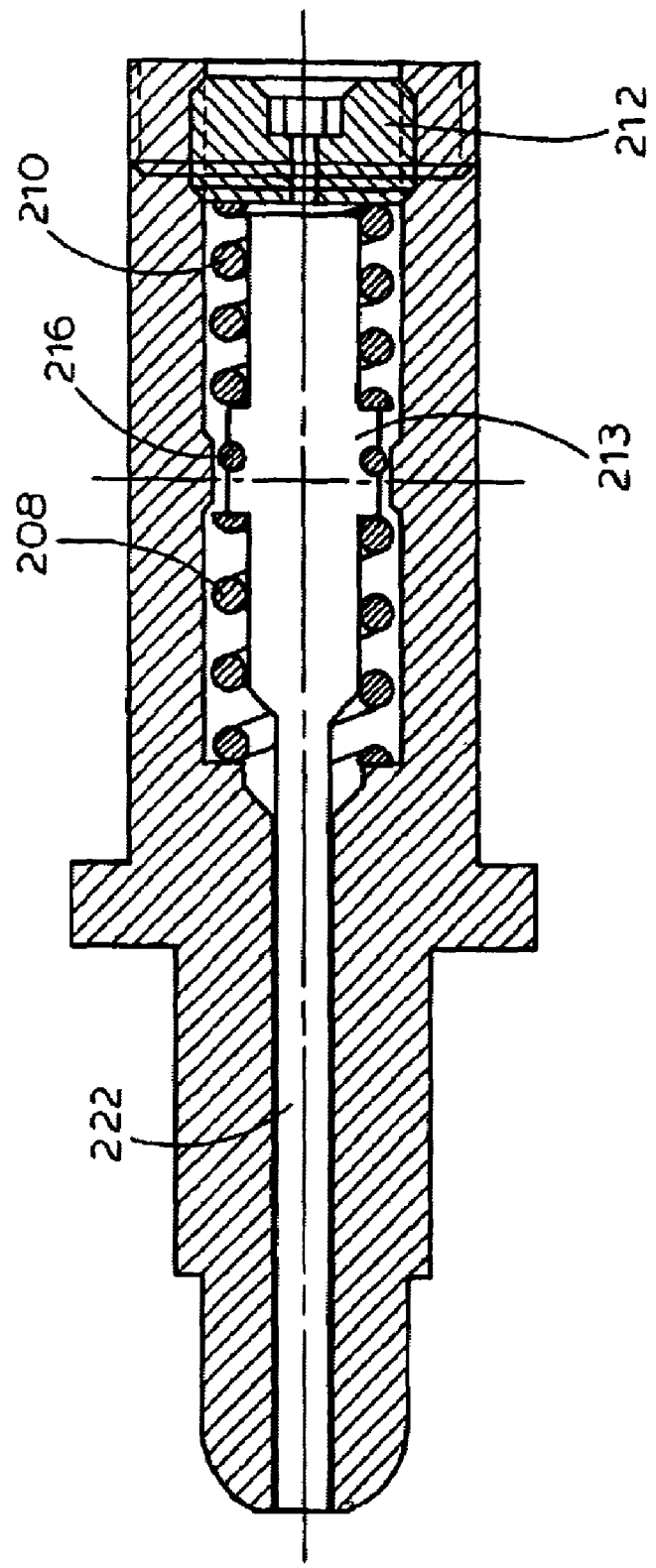

FIG. 4 shows the pressure equalization valve of FIG. 2 in another condition and corresponds to FIG. 17 of the referenced disclosure. Note that the difference between FIGS. 3 and 4 is in the relative positioning of the plunger and seal face. Said plunger position is a function of the direction and magnitude of the instantaneous differential pressure on the valve plunger.

Figure 4A:
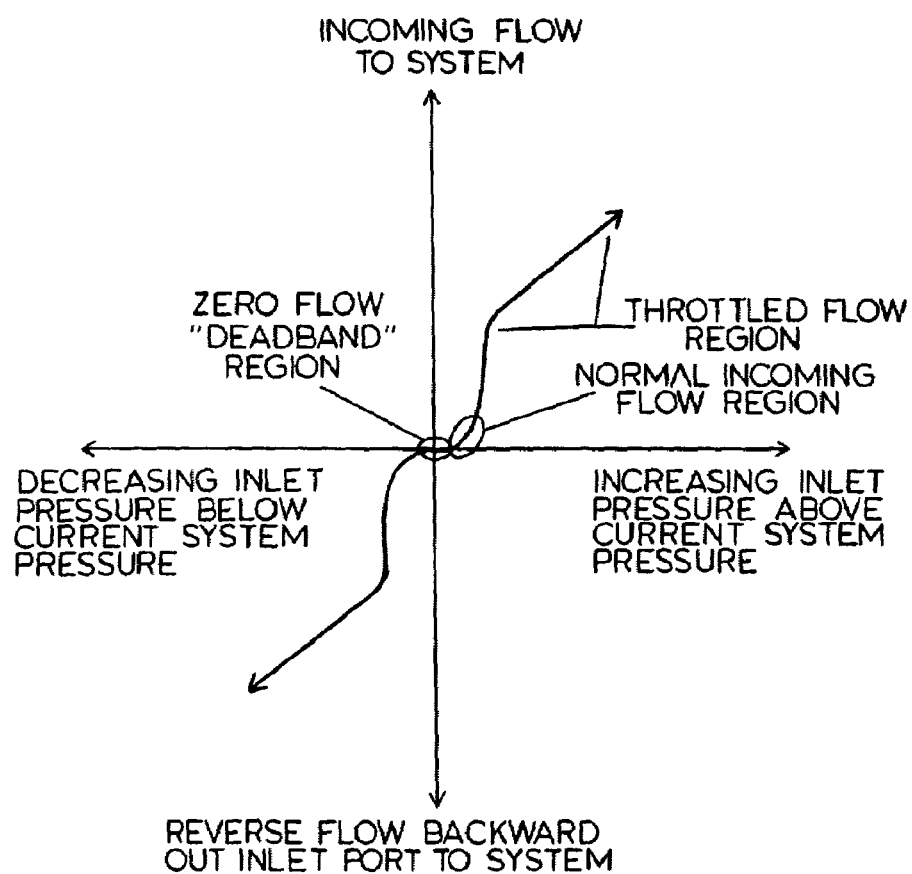

FIG. 4a indicates the relative flow characteristics of the equalizing valve under various differential pressure and flow conditions. Note the deadband region around zero differential pressure indicating that the flow becomes zero before the magnitude of the differential pressure reaches zero.

FIG. 5 shows an alternative form of the equalizing valve embodying the present invention with an O-ring seated on a moving plunger.

FIG. 6 shows an alternative form of the equalizing valve embodying the present invention with an O-ring seated on the stationary valve body.

Figure 7:
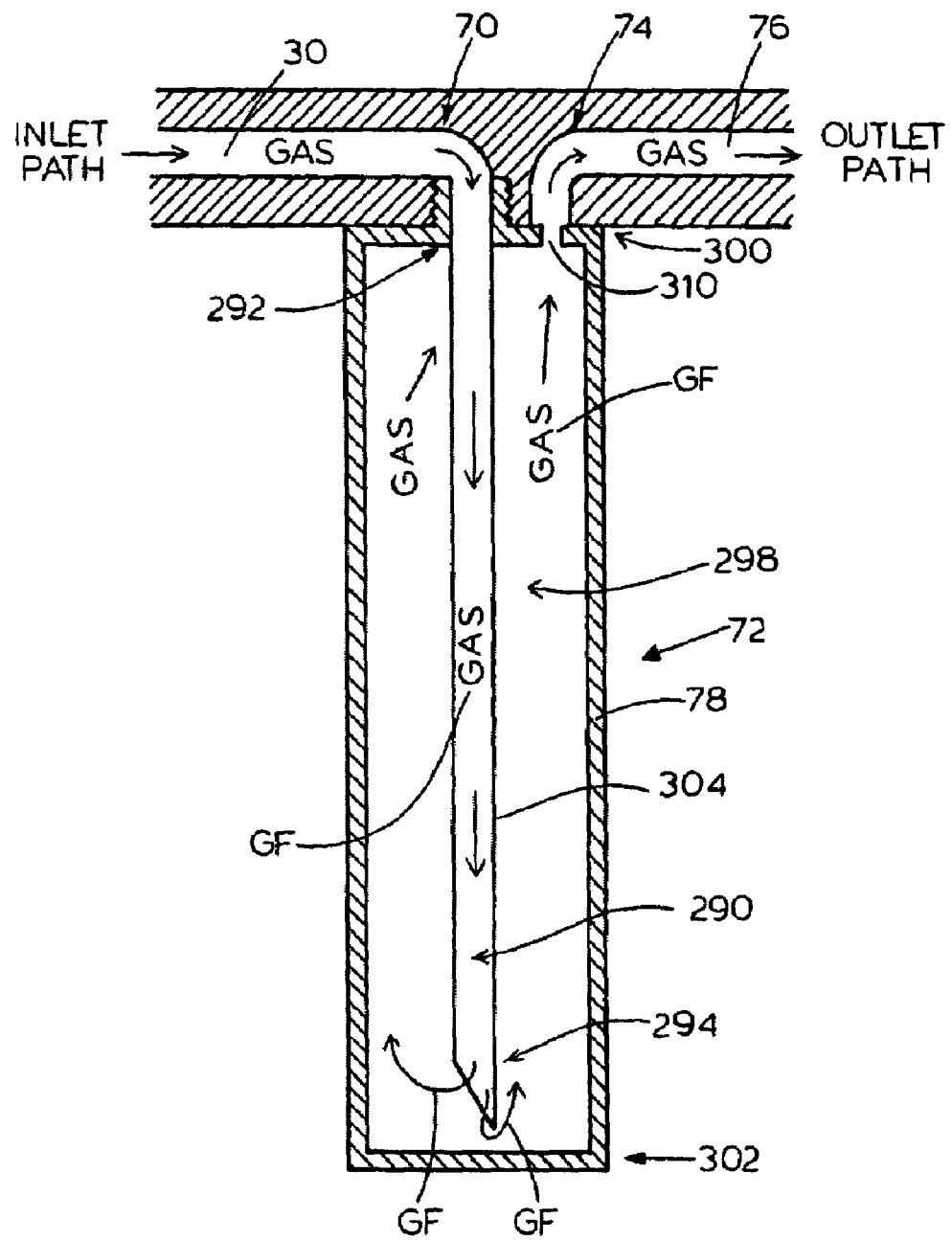

FIG. 7 shows a reservoir used in the system embodying the present invention.

Figure 8:
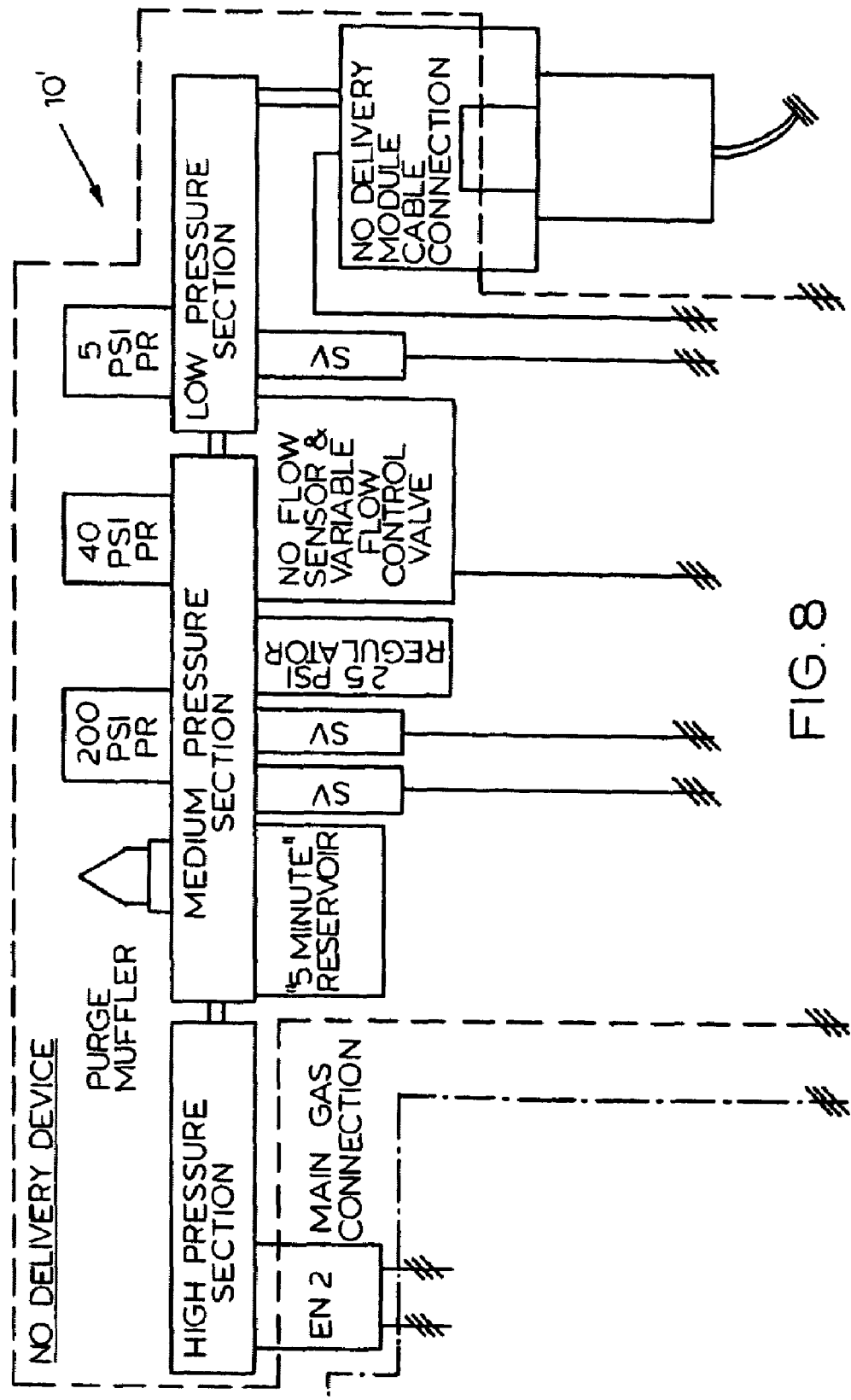
Figure 8A:
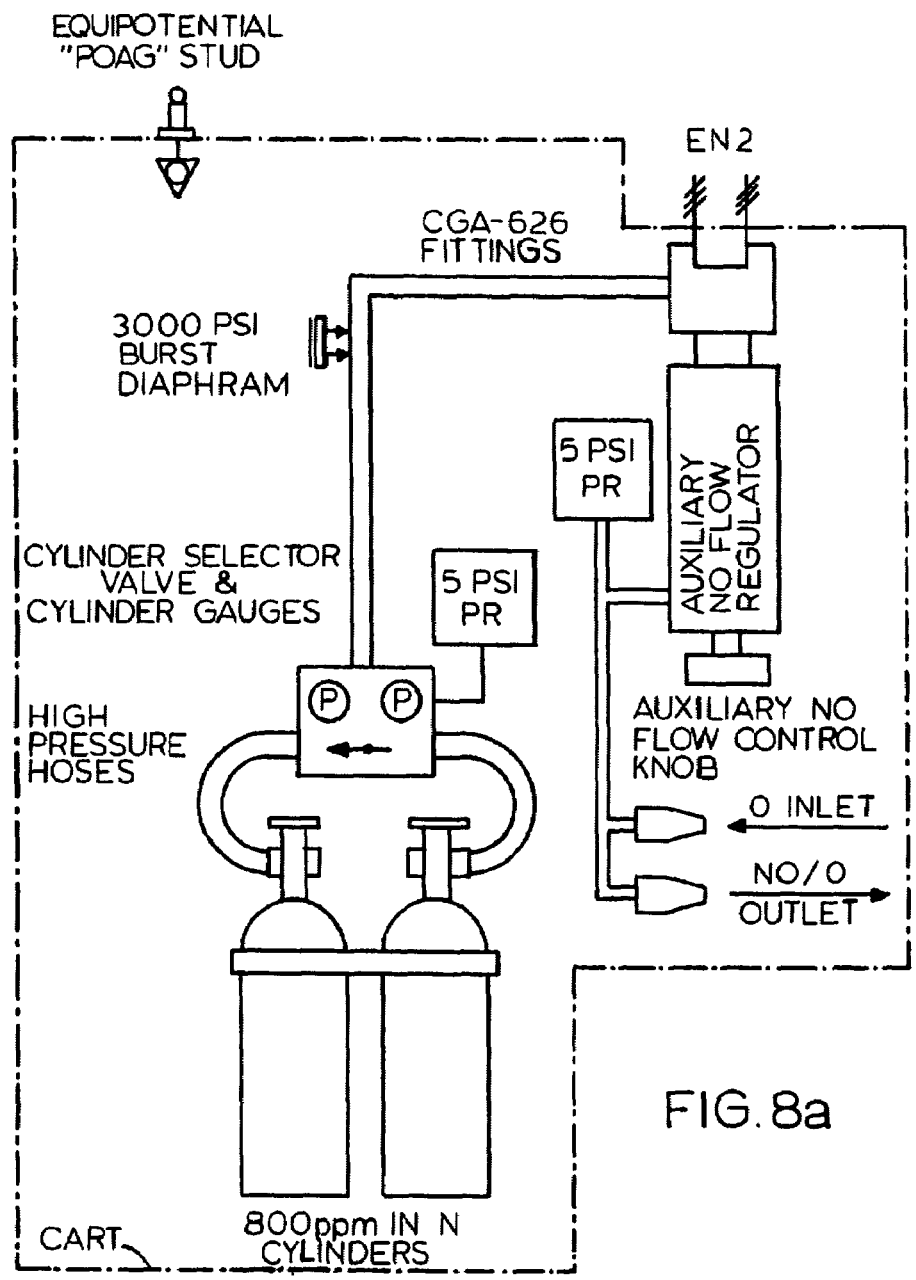
Figure 8B:
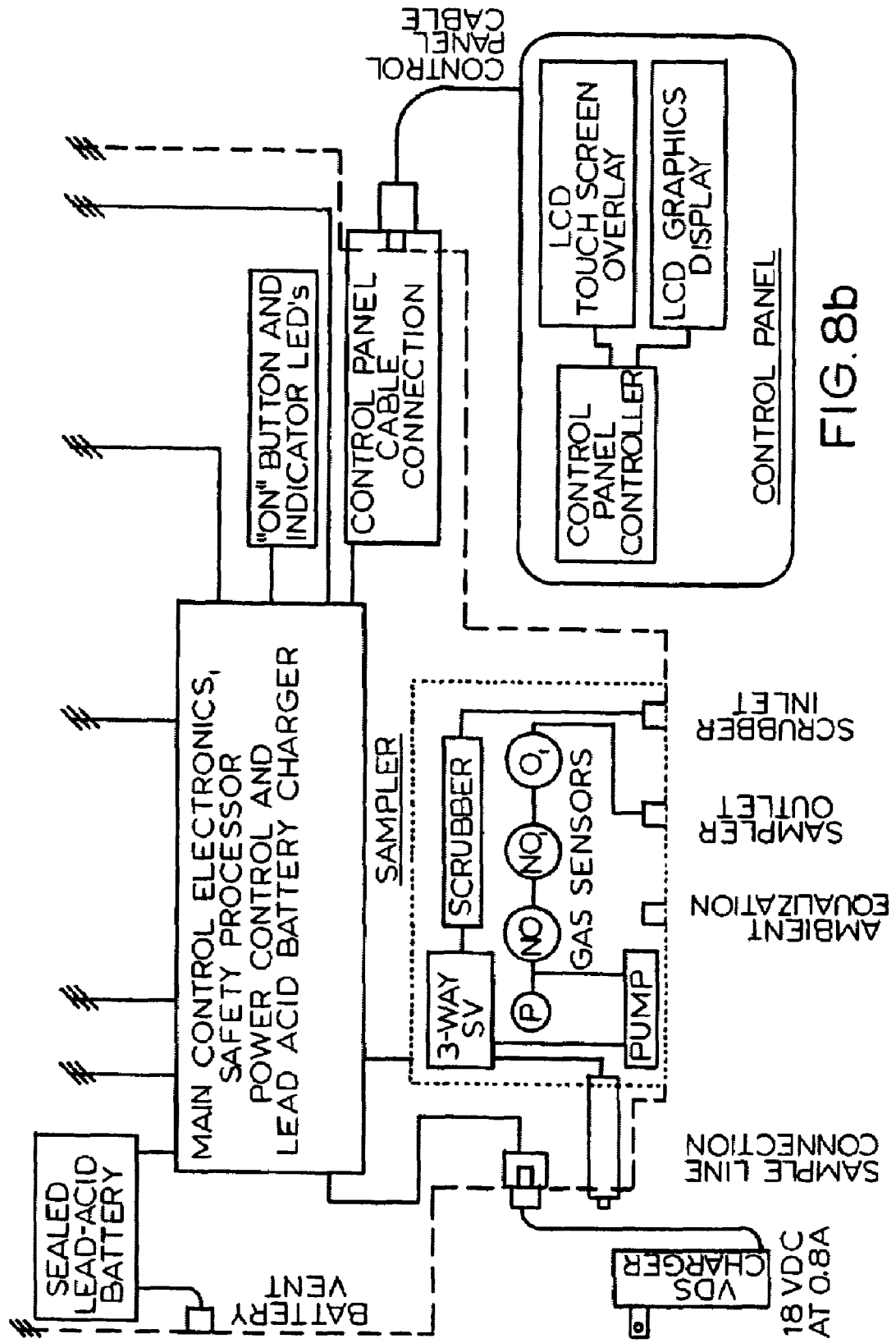
Figure 8C:
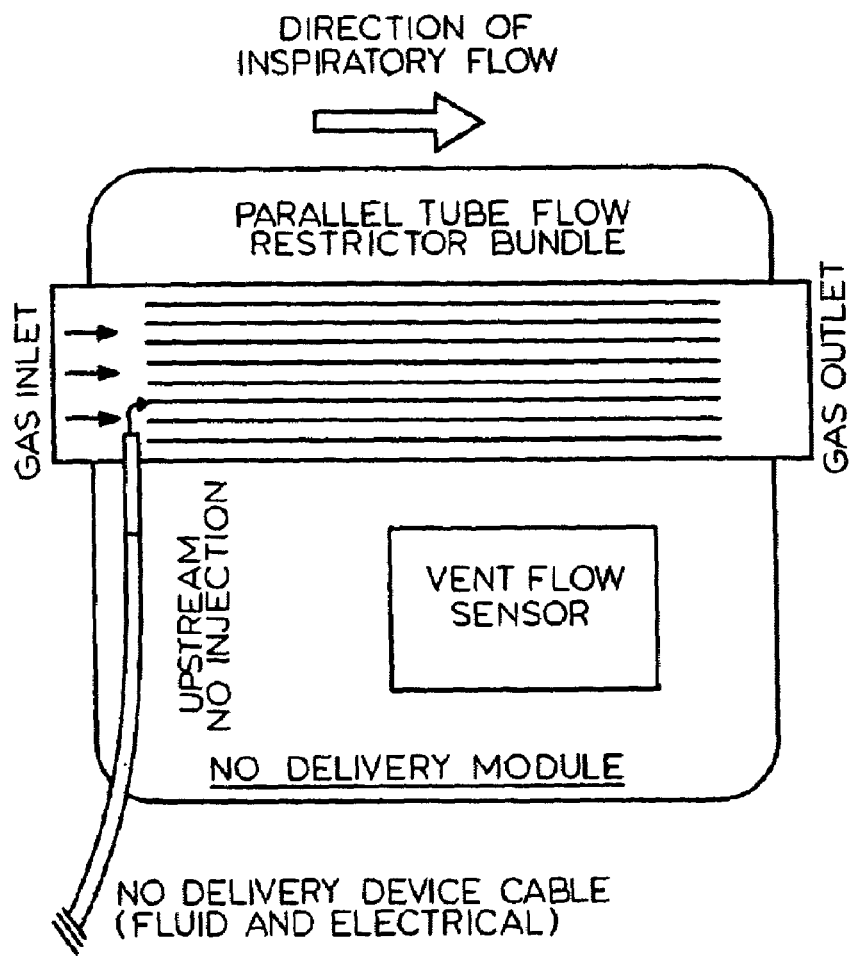

FIG. 8 is a detailed schematic of a system embodying the teaching of the present invention in which circuits for alarms, monitors and the like are indicated.

Figure 1:
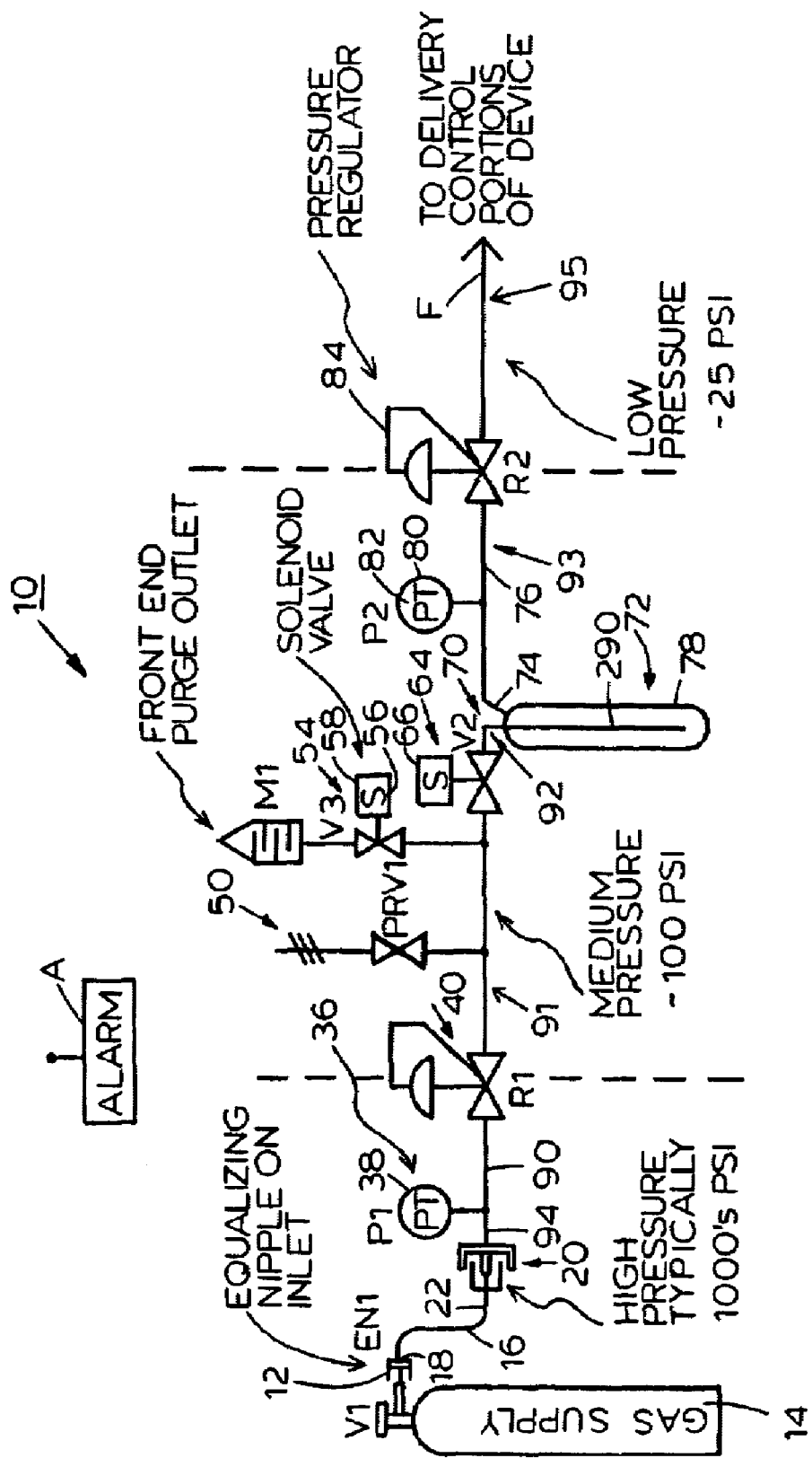
FIG. 1 is an overall schematic of one form of the system embodying the present invention.
Figure 9:
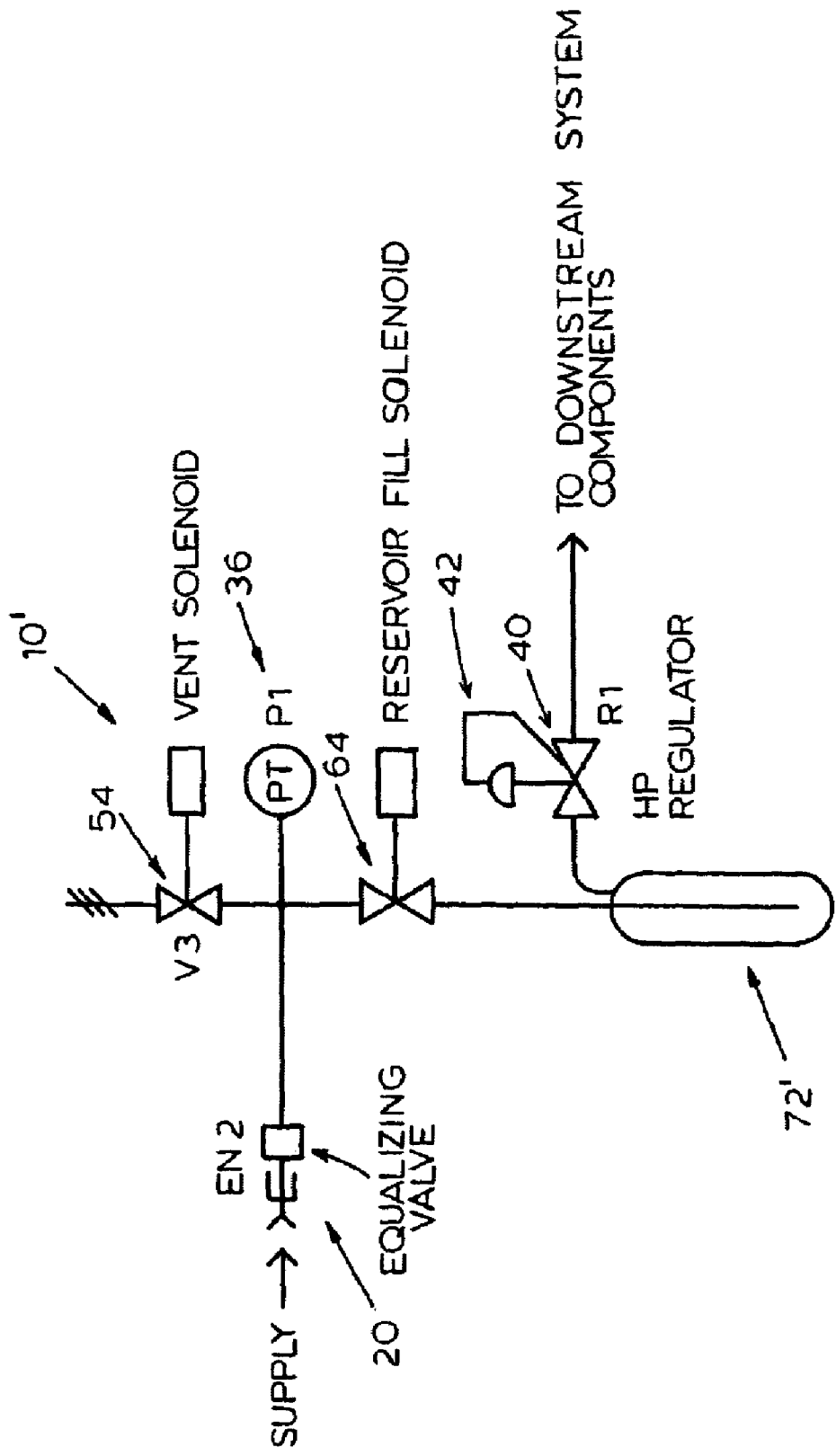

FIG. 9 illustrates an alternative form of the system shown in FIG. 1 with a reservoir located upstream of a first pressure sensor.

Figure 10:
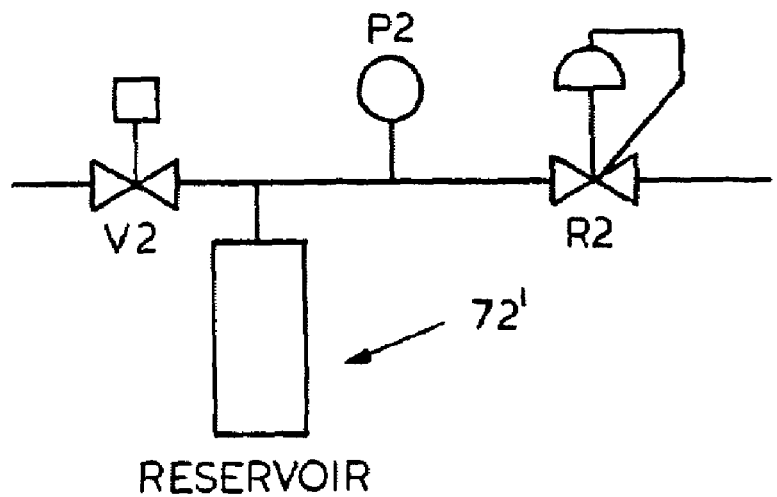

FIG. 10 shows an alternative form of the reservoir unit included in the system embodying the present invention.

Figure 11:
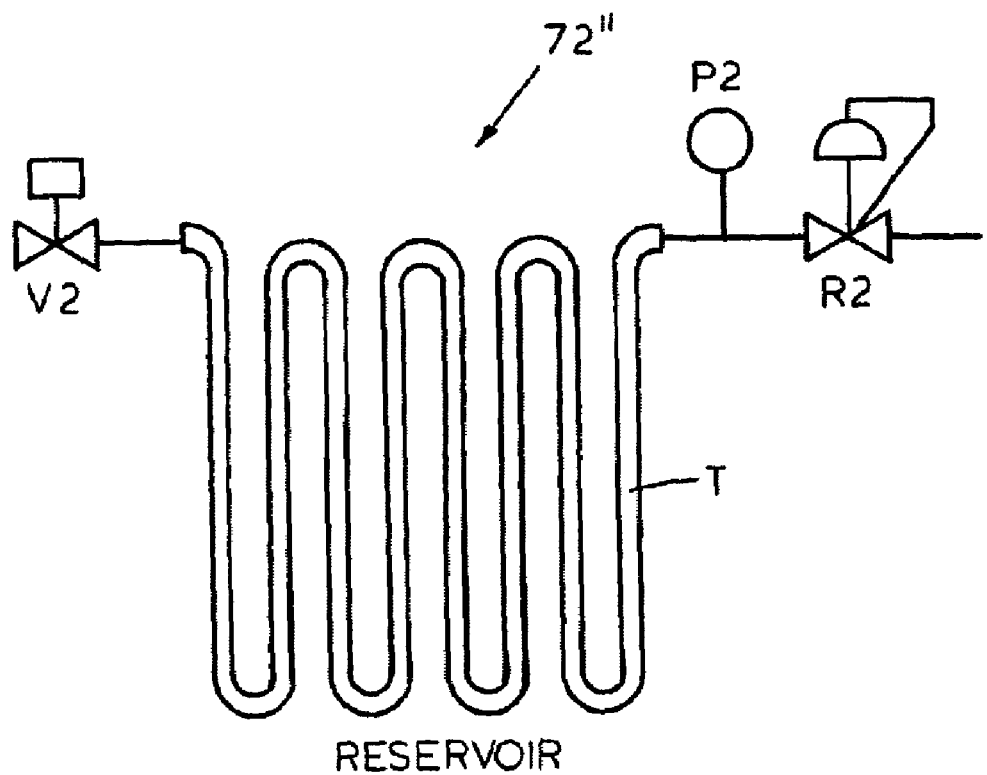

FIG. 11 shows another alternative form of the reservoir unit included in the system embodying the present invention.

DETAILED DESCRIPTION OF THE PREFERRED EMBODIMENT OF THE INVENTION

Other objects, features and advantages of the invention will become apparent from a consideration of the following detailed description and the accompanying drawings.

Broad System

Referring to FIG. 1, the present invention is broadly embodied in a system 10 for use in administrating therapeutic gas to a patient. System 10 comprises a first equalization valve 12 that is fluidically connected to a source 14 of therapeutic gas. A first fluid conduit 16 has an inlet end 18 fluidically connected to the first equalization valve to receive fluid from source 14. For purposes of this disclosure, the terms upstream and downstream as well as source side and system side will be with reference to a flow direction from source 14 toward a patient with the flow direction being indicated in FIG. 1 by arrow F. Other terms, such as inlet and outlet will also be with reference to those flow directions.

As will be discussed below, first equalization valve 12 includes elements to define an equalization pressure between the first fluid conduit and the source of therapeutic gas. The elements are movable to immediately change the position of the equalization valve plunger when there is a change in fluid pressure in either the source of therapeutic gas or in the first fluid conduit to equalize the pressures on either side of the valve. This differs from the action of a check valve which will delay such equalization when the source pressure drops.

System 10 further includes a second equalization valve 20 which is identical to the first equalization valve and operates the same way. Second equalization valve 20 is fluidically connected to outlet end 22 of fluid conduit 16 to receive fluid therefrom. The fluid conduit can include several fluid connections, including several equalization valves and a selector valve, so a plurality of gas sources can be used in place of the single gas source shown in FIG. 1. Such plural connections are not shown for the sake of convenience as those skilled in the art will understand what is required to achieve such plural connections based on the teaching of this disclosure.

System 10 further includes a first fluid manifold 90 which has an inlet end 94 fluidically connected to second equalization valve 20. Second equalization valve 20 includes elements to define an equalization pressure between the first fluid conduit and the first fluid manifold. The elements of equalization valve 20 are movable to immediately change the valve plunger position when there is a change in fluid pressure in either the first fluid conduit or in the first fluid manifold to equalize the pressure on either side of the valve.

A first pressure sensor 36 is fluidically connected to first fluid manifold 90. First pressure sensor 36 includes a signal generator 38 which generates a signal corresponding to fluid pressure in the first fluid manifold adjacent to inlet end 94 of the first fluid manifold. Signal generator 38, like the signal generators and signal receivers discussed in this disclosure can be an off-the-shelf item and the details thereof will not be discussed as those skilled in the art will be able to understand the type and operation of such elements based on the teaching of this disclosure.

A first pressure regulator 40 is fluidically connected to the first fluid manifold. The outlet of the pressure regulator 40 is connected to a second fluid manifold 91. It is noted that elements 16, 90 and 91 can also be referred to as a as well as other elements including, but not limited to, regulator 40.

A pressure relief valve 50 is fluidically connected to the second fluid manifold downstream of the pressure regulator.

A first solenoid controlled valve 54 is fluidically connected to the second fluid manifold and includes a signal receiver 56 which controls operation of the first solenoid controlled valve in accordance with signals received. Valve 54 is controlled by a central processor which opens and closes valve 54 to purge at appropriate times. The central processor receives signals from sensor 36 and includes timing circuits.

A muffler 60 is fluidically connected to said first solenoid controlled valve and vents to atmosphere.

A second solenoid controlled valve 64 is fluidically connected to the second fluid manifold and includes a signal receiver 66 which controls operation of the second solenoid controlled valve in accordance with signals received from, for example, pressure sensor 36. The outlet of valve 64 is connected to the third fluid manifold 92.

The third fluid manifold is fluidically connected to a fluid reservoir unit 72. Inlet end 74 of a fourth fluid manifold 93 is fluidically connected to the fluid outlet of hollow housing 78 of the reservoir. Fluid flowing from the third fluid manifold thus moves through the fluid reservoir and then flows to the fourth fluid manifold. Flow entering the reservoir thus flows in a counterflow direction to fluid exiting the reservoir as will be understood from the following discussion. This counterflow arrangement acts against stagnation of fluid in the reservoir.

A second pressure sensor 80 includes a signal generator 82 and is fluidically connected to the fourth fluid manifold. Alternatively, pressure sensor 80 could be connected to the third fluid manifold rather than to the fourth fluid manifold. Signal generator 82 generates a signal corresponding to fluid pressure of fluid in the fourth fluid manifold.

A second pressure regulator 84 is fluidically connected to the fourth fluid manifold. The outlet of the second pressure regulator 84 is connected to a fifth fluid manifold 95.

An alarm unit A is electrically connected to the signal generators discussed above so an operator will be alerted to the state of the system. The electrical connection can be via electrical connectors or over the air.

Operation of the Broad System

Operation of the broad system 10 is generally as follows. During normal operation with a source of therapeutic gas connected to the system, gas flows through the equalizing valves to the first fluid manifold where the pressure is monitored. The therapeutic gas then flows through the second and third fluid manifolds into fluid reservoir 72 and fluid from the reservoir flows to the patient via the fourth and fifth fluid manifolds.

However, if the pressure in source 14 drops (because, for example, the source is depleted or has been removed for replacement), such pressure drop is immediately passed to the first fluid manifold because of the operation of the equalizing valves and is sensed by pressure. It is noted that as with valve 54, valve 64 is controlled by a central processor. This pressure sensor then generates a signal which causes solenoid controlled valve 64 to close thereby sealing off the system downstream of valve 64 from contamination which may move thereinto when the system is repressurized when a new gas source is connected. Therapeutic gas continues to be supplied to the patient from the reservoir.

When pressure in the first manifold increases as sensed by pressure sensor 36 because, for example, a new source of therapeutic gas is connected to the system, the system upstream of valve 54 will be purged before it is connected to the patient to be sure that any impurities that may have been introduced into the system upstream of valve 54 when the system was not connected to a source of gas are removed before this portion of the system is opened to the patient. The purge is effected by closing valve 64, opening valve 54 and causing therapeutic gas to flow through the system from the source through valve 54 and muffler 60. The central processor sends signals to close valve 54 and open valve 64 after a period of time. Once valve 64 is open, gas flows into the reservoir from the fluid manifold fluidically connected thereto.

An alternative form of the system is shown in FIG. 9 as system 10'. System 10' is similar to the just-discussed system 10 except that reservoir 72' is located upstream of first pressure regulator 40 in system 10'. Second solenoid controlled valve 64 and opening valve 54 are also located upstream of first pressure regulator 40. System 10' operates in a manner similar to system 10 and thus will not be further discussed.

Equalizing Valve

The equalizing valve is discussed in the referenced and incorporated disclosure and this discussion is included herein for the sake of completeness. It is also noted that if more than one equalizing valve is included in the system, all such equalizing valves are similar in function and operation. Thus, only one equalizing valve will be described, it being understood that the description will be applicable to any and all equalizing valves used in the system.

Referring to FIGS. 2, 3 and 4 (which correspond to FIGS. 15, 16 and 17 of the referenced disclosure), a pressure equalization valve 200 is shown that equalizes pressure on the two sides of the valve until the pressure on the high side of the valve is less than or equal to the pressure on the low side plus the difference that will be referred to as the equalization pressure.

The valve may have a symmetrical pressure flow characteristic where the equalization pressure is the same regardless of which side of the valve is high, or it may have an asymmetrical characteristic with a different equalization pressure depending on which side of the valve has the higher pressure. That is: (high side pressure–low side pressure) ≦equalization pressure 1, cylinder pressure is higher than system pressure; (high side pressure–low side pressure) ≦equalization pressure 2, system pressure is higher than cylinder pressure; equalization pressure 1=equalization pressure 2 in the symmetrical case.

Valve 200 is useful as a valve at the inlet of a gas system where a pressurized cylinder is connected as shown in FIG. 2. The equalization valve is connected directly to cylinder valve 202 of cylinder 204.

This valve keeps the system positively pressurized when a cylinder is removed while allowing the system to detect when a cylinder is disconnected and reconnected by monitoring the pressure at a pressure sensor (see FIG. 1 of the referenced document). A normal pressure check valve with the cylinder on the inlet side of the valve would keep the system pressurized when a cylinder is disconnected but would not allow the detection of a cylinder change in all situations. Consider the case where the system is not delivering gas or purging. The pressure on the system side of the check valve would not change when the cylinder was disconnected and then a cylinder of the same or lower pressure was reconnected and the cylinder valve opened. The system could not detect a cylinder change in this scenario.

With the pressure equalization valve, the pressure on the system side of the valve drops to atmospheric pressure plus equalization pressure 2 when a cylinder is removed. The system remains pressurized to greater than atmospheric pressure. When a sufficiently pressurized cylinder is reconnected and the cylinder valve opened, the system pressure rises to the cylinder pressure minus equalization pressure 1. As long as the cylinder pressure is greater than equalization pressure 1+equalization pressure 2, the system can detect the cylinder change.

As shown in FIG. 3, valve 200 includes a plunger 213 housed inside a valve body 206. Two springs 208 and 210 are located on either side of the plunger. A vented set screw or similar functioning mechanical retainer scheme 212 is located on the system side of the valve and retains the plunger and the springs in the valve. The springs are chosen such that the plunger is positioned so that O-ring 216 is positioned somewhere on sealing surface 218 inside the valve body when the spring forces are equal. It is noted that while the present disclosure refers to an O-ring, any suitable seal or seal element can be used without departing from the scope of the present disclosure. The springs may be chosen to give the desired equalization pressures. If the pressure on the system side of the valve is greater than the pressure on the cylinder side by more than equalization pressure 2, the plunger will be pushed toward the cylinder side until the O-ring clears the sealing surface. This is the situation that will occur if the system side of the valve is pressurized to greater than equalization pressure 2 and the cylinder is removed. Gas will then pass through the valve from the system side to the cylinder side.

Valve channel 220 is larger than valve pin 222 so that gas can flow through the channel. The flow rate through the valve is limited by the size of orifice 224. If the flow rate is high, the plunger will seat against plunger stop 226 and flow will be throttled. Gas will flow until the pressure on the system side is equal to the pressure on the cylinder side plus equalization pressure 2. At this point, the O-ring will seat on the sealing surface and gas will cease flowing. The plunger will be positioned as shown in FIG. 3. The plunger pin 222 fills valve channel 220 so that gas will flow through the channel but large debris does not enter the valve from this side. If gas is not flowing on the system side of the valve, then the system side of the valve will remain pressurized at equalization pressure 2.

When pressure on the cylinder side of the valve is raised to greater than the pressure on the system side plus equalization pressure 1, then the plunger will be pushed toward the system side until the O-ring clears the sealing surface. This will happen when a new pressurized gas source is connected. Gas will then flow through the valve until the pressure on the system side equals the pressure on the cylinder side minus equalization pressure 1. At very high flow rates, the plunger will seat against the set screw or similar functioning mechanical retainer scheme and flow will be throttled. Once the pressure on the system side equals the pressure on the cylinder side minus equalization pressure 1, the O-ring will seat against the sealing surface. The plunger will be positioned as shown in FIG. 4.

As can be understood from FIG. 3, valve body 206 of the equalizing valve includes a first bore 250 having an inner dimension 252 and a second bore 254 having an inner dimension 256. Inner dimension 256 is larger than inner dimension 252 and a shoulder 258 is defined at the intersection of bore 250 and bore 254. Shoulder 258 is tapered and defines plunger stop 226. Shoulder 258 is located on first end 262 of the second bore which has a second end 264 on which the set screw is mounted. Spring 208 has a first end 266 in abutting contact with the first end of bore 254 and a second end 268 in abutting contact with the plunger. Spring 210 has a first end 270 in abutting contact with the plunger and a second end 272 in abutting contact with the set screw adjacent to the orifice. Plunger 213 has a first end 280 of the first portion of the plunger and a second end 282 of the first end as well as a first end 284 of the second portion of the plunger and a second end 286 of the second portion of the plunger. A longitudinal axis 290 extends between first end 280 and second end 286 of the plunger.

It should be noted that although the bore and plunger cross sections are nominally shown as circular, the functions may be preserved by other cross sectional geometries as long as the associated passages for gas flow and sealing surfaces are maintained. For example, the plunger and bore could be fabricated with a hexagonal or rectangular cross section without changing the underlying operation of the equalizing valve. In addition, although specific reference in this discussion is made to O-ring seals, this does not preclude the use of other sliding or face seal mechanisms consistent with the general art. For example, properly honed and matched hard surface seals could be incorporated in versions of the equalizing valve where O-rings would be undesirable due to material compatibility problems or where the O-rings could become abraded under severe service.

Several key features of valve 200 are as follows.

|cylinder side pressure−system side pressure|≦equalization pressure when there is no flow. Where the equalization pressure may depend on which side of the valve is at higher pressure.

The system side is kept pressurized when a cylinder is removed as long as gas does not flow from the system side (away from the valve). This helps preserve the cleanliness of the system side circuit.

The pin almost fills the cylinder side of the valve. This has two advantages: this reduces the possibility of debris entering the valve; and reduces the dead space where contaminating gas can be trapped during cylinder changing.

The orifice limits the flow rate through the valve.

Several variations of valve 200 are possible within the scope of the teaching of the present disclosure. As already mentioned, the equalization pressure may or may not be different when the pressure is greater on the system side than it is when the pressure on the cylinder side is greater. This can be accomplished in several ways. For example, the spring constants of the two springs can be varied. Alternatively, the position and shape of the sealing surface can be altered.

Still further variations of valve 200 are indicated in FIGS. 5 and 6, with valve 200' in FIG. 6 including a plunger 213' which is cylindrical and has a continuous cylindrical wall 230 that is continuous from end 232 to end 234 of the plunger. O-ring 216' fits in a groove defined in cylindrical wall 230. Valve 200" in FIG. 6 includes a plunger 213" which is cylindrical and has a wall 230" that includes shoulders 236 and 238 adjacent to end 232" and end 234" respectively of plunger 213". O-ring 216" fits in a groove defined in wall 240 of valve body 206". Wall 240 is continuous and cylindrical.

It can be understood from the foregoing disclosure and from the teaching of the referenced disclosure that the equalizing valve of the present invention provides a low dead volume pressure equalizing device that provides a flow versus pressure dead band that provides for zero flow in either direction at non-zero differential pressures. The dead band may be symmetric or asymmetric in differential pressure about zero with respect to a non-zero flow in either direction through the valve. As can be seen in the figures, the pin is sized to minimize the dead space and the springs have their spring characteristics, including the length as well as the force versus displacement characteristics of the springs so the plunger is located in an intermediate region of plunger travel when flow is prohibited and so the dead band is either symmetric or asymmetric in differential pressure about zero with respect to non-zero flow in each direction. As can also be understood from the foregoing disclosure, the valve can incorporate a progressive flow restriction safety mechanism that prevents high flow rates in the event of an otherwise unconstrained flow.

Reservoir

Reservoir 72 is shown in FIGS. 1 and 7. As shown, reservoir 72 comprises a dip tube 290 which has a fluid inlet end 292 fluidically connected to outlet end 70 of third fluid manifold 92 and an outlet end 294 spaced apart from the inlet end of the dip tube. Hollow housing 78 of the reservoir has an internal volume 298, a first end 300, a second end 302 spaced apart from first end 300 of the hollow housing and a longitudinal axis 304 extending between first end 300 of the hollow housing of the fluid reservoir and second end 302 of the hollow housing of the fluid reservoir. The dip tube is located in the internal volume of the hollow housing of the reservoir and extends in the direction of longitudinal axis 304 of the hollow housing. The outlet end of the dip tube is located adjacent to second end 302 of the hollow housing inside that hollow housing. A fluid outlet 310 is defined in the hollow housing adjacent to first end 300 of the hollow housing and is spaced apart from the second end of the hollow housing. Outlet 310 is fluidically connected to inlet end 74 of the fourth manifold 76 whereby gas flowing from outlet 310 flows into the fourth fluid manifold.

Therapeutic gas flows through the dip tube and out of the end of the dip tube near the second end of the housing. This gas then flows outside of the dip tube in a direction opposite to the gas flowing inside the dip tube and out of outlet 310 and into the fourth fluid manifold. This gas flow is indicated in FIG. 7 by arrows GF. The counterflow pattern of the therapeutic gas through the hollow housing helps prevent the gas from stagnating in the remote end of the reservoir. The housing can be equipped with state sensors, such as pressure sensors and can also be equipped with flow sensors that are electrically connected to gauges that inform an operator of conditions existing inside the reservoir. The sensors can also be electrically connected to alarms to alert an operator of undesired conditions in the reservoir. Emptying of the reservoir may be one undesired condition and stagnation may be another such undesired condition while leaks may be yet another undesired condition. Sensors can also be attached to the reservoir to be connected to various alarms and indicators to alert an operator of the operating status of the reservoir such as full, filling, emptying, purging and the like as well as the remaining amount of gas in the reservoir.

Several other alternative forms of the reservoir are also possible within the scope of the present invention. One alternative form of the reservoir unit does not include a dip tube and another form is shown in FIG. 10 as reservoir 72' and has the reservoir inlet also being the reservoir outlet so that fluid flowing into and out of the reservoir flows through the same port. Yet another alternative form of the reservoir is shown in FIG. 11 as reservoir 72" and which includes a coiled tube T which tends to prevent the stagnation of gas in the reservoir.

Technical Application

System 10' is shown in FIG. 8 and includes appropriate electrical connections as well as alarms and sensors and fluidic connections for two source gases. A selector valve selects one of the two cylinders to provide gas for the patient. An alternative form of the system would include only a single source cylinder without the plumbing for a second cylinder and without a cylinder selector valve. System 10' carries $NO/N_2$ from the selected source cylinder normally mounted on a cart to the patient circuit as follows. Gas flows from the cylinder at nominally 800 ppm NO (in $N_2$ balance) through the CGA-626 cylinder fittings on the flexible high pressure hose to a pressure gauge, then through the cylinder selector valve and plumbing on the cart into the inlet (Main Gas Connection) of the NO delivery device. The cart plumbing includes equalization valves in the CGA-626 cylinder fittings, a purge line with a five psi relief valve connected to the selector valve, a safety burst diaphragm and an ancillary flow regulator for use with a manual resuscitator. The gas in these sections of the system is at roughly supply cylinder pressure except in the purge line, where the pressure is between the cylinder pressure and the five psi relief pressure. The gas can be selected to flow though the ancillary flow regulator on the cart (Manual NO delivery system) to be used with a manual resuscitator while simultaneously maintaining the gas supply to the NO delivery device. In this instance, the cart may also be supplied with flow regulated $O_2$ to supply the dilution and/or breathing gas for the patient for manual resuscitation.

Once the gas enters the NO delivery device, it passes through the high pressure section. This section contains the CGA-626 inlet nipple, equalization valve and an integrated high-pressure step down regulator delivering 120 psi to the next stage. The main gas connection is supplied with a hand-tightening nut and is followed by a 10 micron gas filter to prevent debris from entering the device. Also included in this section is a 3000 psi electronic pressure gauge to monitor the input pressure and to detect supply pressure changes consistent with changing gas supply between sources.

Next in the $NO/N_2$ gas circuit is the medium pressure section that incorporates a five minute reservoir, several solenoid valves, a purge muffler, two safety pressure reliefs and a 25 psi step down regulator. The valves are operated by the main control processor and are used to isolate the gas input to the reservoir, purge the NO delivery device gas circuit upstream of the purge valve or direct gas into the reservoir. The gas stored in the reservoir supplies the system during routine device purges, or in the case of both cylinders being allowed to run empty, will give the operator a few minutes to attache and activate other sources or a back-up system before the system stops the delivery of $NO/N_2$. This reservoir is a self-flushing design with a dip tube so that gas within it is continuously renewed during normal delivery operation. Additionally, if the system is inactive for a significant period, this reservoir is fully purged at the next attempted use.

The medium pressure section is equipped with two safety reliefs. The first pressure relief, with a 200 psi opening point, is included to protect the reservoir in the event of a failure in the high pressure section. The gas is further pressure reduced by a 25 psi regulator prior to the gas entering the low pressure section. This regulator is followed by a 40 psi pressure relief, intended as protection for downstream components. The embodiment shown in FIG. 8 is intended to be illustrative only and it is noted that some of the components shown in FIG. 8 can be located in positions different from those shown in FIG. 8 without departing from the scope of this disclosure.

It is noted that while one reservoir housing is shown, a plurality of housings can be used and fluidically interconnected with each other and with the remainder of the system to perform the function of the reservoir. The reservoir can also be separated into sections located in various pressure stages, including a high pressure stage, such as indicated in FIG. 1 as stage HP adjacent to the source of gas, a medium pressure stage MP and a low pressure stage LP on the patient side of the system. The reservoir can be operated at pressures significantly higher than ambient pressure, if desired, including operation at the full supply pressure, with a suitable rearrangement of the orientation of a high pressure regulator, the vent solenoid and reservoir solenoid and the reservoir, as shown in FIG. 9. If desired, the reservoir can be one large volume that can contain typically as much as five minutes gas supply. However, adding housings may increase this time if desired. In practice, there is no specific limit on the size of the reservoir or reservoirs.

It is noted that the alarms and sensors of system 10 are designed and connected to automatically isolate the reservoir if the supply pressure drops below a preset level and then warn the user that the system is operating on the reservoir. The user will then be alerted to change the source.

It is understood that while certain forms of the present invention have been illustrated and described herein, it is not to be limited to the specific forms or arrangements of parts described and shown.

The invention claimed is:

1. A system for use in administrating therapeutic gas to a patient comprising:
    A) a source of therapeutic gas;
    B) a first equalization valve having an inlet and an outlet;
    C) a first fluid conduit having an inlet end fluidically connected to said first equalization valve;
    D) said first equalization valve having an inlet and an outlet and including elements to define a first equalization pressure and a second equalization pressure between the inlet and the outlet of said first equalization valve, with the elements being movable to immediately allow flow of gas through said first equalization valve when pressure at the inlet of said first equalization valve is greater than pressure at the outlet of said first equalization valve plus the first equalization pressure, or the pressure at the outlet of said first equalization valve is greater than pressure at the inlet of said first equalization valve plus the second equalization pressure, and to prevent flow through said first equalization valve at all other pressure conditions;
    E) a second equalization valve having an inlet and an outlet with the inlet of said second equalization valve being fluidically connected to the outlet of said first fluid conduit;
    F) a first fluid manifold having an inlet end fluidically connected to said second equalization valve;
    G) said second equalization valve having an inlet and an outlet and including elements to define a first equalization pressure and a second equalization pressure between the inlet and the outlet of said second equalization valve, with the elements being movable to immediately allow flow of gas through said second equalization valve when pressure at the inlet of said second equalization valve is greater than pressure at the outlet of said second equalization valve plus the first equalization pressure of said second equalization valve, or the pressure at the outlet of said second equalization valve is greater than pressure at the inlet of said second equalization valve plus the second equalization pressure of said second equalization valve, and to prevent flow through said second equalization valve at all other pressure conditions;

H) a first pressure sensor fluidically connected to said first fluid manifold, the first pressure sensor including a signal generator which generates a signal corresponding to fluid pressure in said first fluid manifold;

I) a first pressure regulator fluidically connected to said first fluid manifold and fluidically connected to a second fluid manifold;

J) a pressure relief valve fluidically connected to said second fluid manifold;

K) a first solenoid controlled valve fluidically connected to said second fluid manifold, said first solenoid controlled valve including a mechanism which controls operation of said first solenoid controlled valve in accordance with signals received;

L) a muffler fluidically connected to said first solenoid controlled valve;

M) a second solenoid controlled valve fluidically connected to said second fluid manifold, said second solenoid controlled valve being controlled in accordance with signals received and being fluidically connected to a third fluid manifold;

N) an outlet end of said first fluid manifold;

O) a fluid reservoir unit having an outlet;

P) a fourth fluid manifold having an inlet end fluidically connected to the outlet of said fluid reservoir unit;

Q) a second pressure sensor fluidically connected to said fourth fluid manifold and including a signal generator which generates a signal corresponding to fluid pressure of fluid in said fourth fluid manifold; and R) a second pressure regulator fluidically connected to said fourth fluid manifold.

2. The system defined in claim 1 wherein said fluid reservoir unit includes a portion of coiled tubing.

3. A system for use in administrating therapeutic gas to a patient comprising:

A) an equalization valve which includes
  (1) a valve body having a first end and a second end,
  (2) a longitudinal axis extending between the first end and the second end of the valve body,
  (3) a first bore portion extending from the first end of the valve body toward the second end of the valve body,
  (4) a second bore portion intersecting the first bore and extending from the first bore to the second end of the body, the second bore having a second end,
  (5) a plunger stop shoulder defined at the intersection of the first bore and the second bore,
  (6) a sealing surface defined on the valve body adjacent to the second bore,
  (7) an orifice which is fluidically connected to the second bore portion,
  (8) a plunger movably mounted in the valve body and which includes
    (a) a first portion movably located in the first bore portion,
    (b) a second portion movably located in the second bore portion, the first portion of the plunger being joined to the second portion of the plunger,
    (c) a plunger shoulder formed where the first portion of the plunger joins the second portion of the plunger,
    (d) a seal element engagement surface on the second portion of the plunger, and
    (e) a second end on the second portion of the plunger, the second end being spaced apart from the plunger shoulder in the direction of the orifice,
  (9) seal interposed between the seal engagement surface on the plunger and the sealing surface defined on the valve body,
  (10) a first spring located in the second bore portion and having a first end engaged with the second bore portion adjacent to the intersection of the first bore portion and the second bore portion and a second end engaged with the valve plunger, the first spring biasing the valve plunger in a direction toward the orifice,
  (11) a second spring located in the second bore portion and having a first end engaged with the valve plunger and a second end engaged with a surface located adjacent to the orifice, the second spring biasing the valve plunger in a direction toward the first bore portion in opposition to the bias on the valve plunger by the first spring, and
  (12) the plunger being movable in the valve body from a first location in which the plunger shoulder of the plunger is in abutting contact with the plunger stop of the valve body and a second location in which the second end on the second portion of the plunger is in abutting contact with the surface adjacent to the orifice; and B) a fluid reservoir unit which includes
  (1) a dip tube having a fluid inlet end fluidically connected to an outlet end of a fluid manifold and an outlet end spaced apart from the inlet end of said dip tube,
  (2) a hollow housing having an internal volume, a first end, a second end spaced apart from the first end of the hollow housing and a longitudinal axis extending between the first end of the hollow housing of said fluid reservoir and the second end of the hollow housing of said fluid reservoir, the dip tube being located in the internal volume of the hollow housing of said reservoir and extending in the direction of the longitudinal axis of the hollow housing of said reservoir, the outlet end of the dip tube being located adjacent to the second end of the hollow housing of said reservoir, and
  (3) a fluid outlet defined in the hollow housing of said reservoir adjacent to the first end of the hollow housing, the fluid outlet defined in the hollow housing being fluidically connected to another fluid manifold.

4. A system for use in administrating therapeutic gas to a patient comprising:

A) a first equalization valve which includes
  (1) a valve body having a first end and a second end,
  (2) a longitudinal axis extending between the first end and the second end of the valve body,
  (3) a first bore extending from the first end of the valve body toward the second end of the valve body, the first bore having an internal dimension,
  (4) a second bore intersecting the first bore and extending from the first bore to the second end of the body, the second bore having a second end and an internal dimension that is larger than the internal dimension of the first bore,
  (5) a plunger stop shoulder defined at the intersection of the first bore and the second bore, (6) a sealing surface defined on the valve body adjacent to the second bore, (7) a mechanical retainer mounted on the body adjacent to the second end of the second bore, the mechanical retainer including an orifice which is fluidically connected to the second bore, (8) a plunger movably mounted in the valve body and which includes (a) a first portion movably located in the first bore and including an outer dimension, (b) a second portion movably located in the second bore and including an outer dimension, the outer dimension of the second portion of the plunger being larger than the outer dimension of the first portion of the plunger, the first portion of the plunger being joined to the second portion of the plunger, (c) a plunger shoulder formed where the first portion of the plunger joins the second portion of the plunger, (d) an seal engagement surface on the second portion of the plunger, and (e) a second end on the second portion of the plunger, the second end being spaced apart from the plunger shoulder in the direction of the mechanical retainer, (9) a seal element interposed between the seal engagement surface on the plunger and the sealing surface defined on the valve body,

(10) a first spring located in the second bore and having a first end engaged with the second bore adjacent to the intersection of the first bore and the second bore and a second end engaged with the valve plunger, the first spring biasing the valve plunger in a direction toward the mechanical retainer,

(11) a second spring located in the second bore and having a first end engaged with the valve plunger and a second end engaged with the mechanical retainer, the second spring biasing the valve plunger in a direction toward the first bore in opposition to the bias on the valve plunger by the first spring, and

(12) the plunger being movable in the valve body from a first location in which the plunger shoulder of the plunger is in abutting contact with the plunger stop of the valve body and a second location in which the second end on the second portion of the plunger is in abutting contact with the mechanical retainer adjacent to the orifice in the mechanical retainer;

B) a first fluid conduit having an inlet end fluidically connected to the second bore of the valve body and an outlet end;

C) a first fluid manifold having an inlet end fluidically connected to the outlet end of the first fluid conduit;

D) a first pressure sensor fluidically connected to said first fluid manifold, the first pressure sensor including a signal generator which generates a signal corresponding to fluid pressure in said first fluid manifold;

E) a first pressure regulator having an inlet fluidically connected to said first fluid manifold and having an outlet fluidically connected to second fluid manifold;

F) a pressure relief valve fluidically connected to said second fluid manifold;

G) a first solenoid controlled valve fluidically connected to said second fluid manifold;

H) a muffler fluidically connected to said first solenoid controlled valve;

I) a second solenoid controlled valve having an inlet fluidically connected to said second fluid manifold and having an outlet fluidically connected to a third fluid manifold, said second solenoid controlled valve including a signal receiver which controls operation of said second solenoid controlled valve in accordance with signals received;

J) a fluid reservoir unit which includes (1) a dip tube having a fluid inlet end fluidically connected to an outlet end of said third fluid manifold and an outlet end spaced apart from the inlet end of said dip tube, (2) a hollow housing having an internal volume, a first end, a second end spaced apart from the first end of the hollow housing and a longitudinal axis extending between the first end of the hollow housing of said fluid reservoir unit and the second end of the hollow housing of said fluid reservoir unit, the dip tube being located in the internal volume of the hollow housing of said reservoir unit and extending in the direction of the longitudinal axis of the hollow housing of said fluid reservoir unit, the outlet end of the dip tube being located adjacent to the second end of the hollow housing of said fluid reservoir unit, and (3) a fluid outlet defined in the hollow housing of said reservoir adjacent to the first end of the hollow housing and spaced apart from the second end of the hollow housing;

K) a fourth fluid manifold having an inlet end fluidically connected to the fluid outlet of the hollow housing of said fluid reservoir unit;

L) a second pressure sensor fluidically connected to said fourth fluid manifold and including a signal generator which generates a signal corresponding to fluid pressure of fluid in said fourth fluid manifold; and M) a second pressure regulator fluidically connected to said fourth fluid manifold.

5. A system for use in administrating therapeutic gas to a patient comprising:

A) a first equalization valve which includes (1) a valve body having a first end and a second end, (2) a longitudinal axis extending between the first end and the second end of the valve body, (3) a first bore extending from the first end of the valve body toward the second end of the valve body, the first bore having an internal dimension, (4) a second bore intersecting the first bore and extending from the first bore to the second end of the body, the second bore having a second end and an internal dimension that is larger than the internal dimension of the first bore, (5) a plunger stop shoulder defined at the intersection of the first bore and the second bore, (6) a sealing surface defined on the valve body adjacent to the second bore, (7) a mechanical retainer mounted on the body adjacent to the second end of the second bore, the mechanical retainer including an orifice which is fluidically connected to the second bore, (8) a plunger movably mounted in the valve body and which includes (a) a first portion movably located in the first bore and including an outer dimension, (b) a second portion movably located in the second bore and including an outer dimension, the outer dimension of the second portion of the plunger being larger than the outer dimension of the first portion of the plunger, the first portion of the plunger being joined to the second portion of the plunger,
(c) a plunger shoulder formed where the first portion of the plunger joins the second portion of the plunger,
(d) a seal engagement surface on the second portion of the plunger, and
(e) a second end on the second portion of the plunger, the second end being spaced apart from the plunger shoulder in the direction of the mechanical retainer,
(9) a seal interposed between the seal engagement surface on the plunger and the sealing surface defined on the valve body,
(10) a first spring located in the second bore and having a first end engaged with the second bore adjacent to the intersection of the first bore and the second bore and a second end engaged with the valve plunger, the first spring biasing the valve plunger in a direction toward the mechanical retainer,
(11) a second spring located in the second bore and having a first end engaged with the valve plunger and a second end engaged with the mechanical retainer, the second spring biasing the valve plunger in a direction toward the first bore in opposition to the bias on the valve plunger by the first spring, and
(12) the plunger being movable in the valve body from a first location in which the plunger shoulder of the plunger is in abutting contact with the plunger stop of the valve body and a second location in which the second end on the second portion of the plunger is in abutting contact with the mechanical retainer adjacent to the orifice in the mechanical retainer;
B) a first fluid conduit having an inlet end fluidically connected to the second bore of the valve body and an outlet end;
C) a first fluid manifold having an inlet end fluidically connected to the outlet end of said fluid conduit;
D) a first pressure sensor fluidically connected to said first fluid manifold, the first pressure sensor including a signal generator which generates a signal corresponding to fluid pressure in said first fluid manifold;
E) a first pressure regulator having an inlet fluidically connected to said first fluid manifold and having an outlet fluidically connected to a second fluid manifold;
F) a pressure relief valve fluidically connected to said second fluid manifold;
G) a first solenoid controlled valve fluidically connected to said second fluid manifold, said first solenoid controlled valve being controlled in accordance with signals received;
H) a muffler fluidically connected to said first solenoid controlled valve;
I) a second solenoid controlled valve having an inlet fluidically connected to said second fluid manifold and having an outlet fluidically connected to a third fluid manifold, said second solenoid controlled valve including a signal receiver which controls operation of said second solenoid controlled valve in accordance with signals received;
J) a fluid reservoir unit which includes
(1) a dip tube having a fluid inlet end fluidically connected to said outlet end of said third fluid manifold and an outlet end spaced apart from the inlet end of said dip tube,
(2) a hollow housing having an internal volume, a first end, a second end spaced apart from the first end of the hollow housing and a longitudinal axis extending between the first end of the hollow housing of said fluid reservoir unit and the second end of the hollow housing of said fluid reservoir unit, the dip tube being located in the internal volume of the hollow housing of said fluid reservoir unit and extending in the direction of the longitudinal axis of the hollow housing of said fluid reservoir unit, the outlet end of the dip tube being located adjacent to the second end of the hollow housing of said fluid reservoir unit, and
(3) a fluid outlet defined in the hollow housing of said fluid reservoir unit adjacent to the first end of the hollow housing and spaced apart from the second end of the hollow housing;
K) a fourth fluid manifold having an inlet end fluidically connected to the fluid outlet of the hollow housing of said fluid reservoir unit;
L) a second pressure sensor fluidically connected to said fourth fluid manifold and including a signal generator which generates a signal corresponding to fluid pressure of fluid in said fourth fluid manifold; and
M) a second pressure regulator fluidically connected to said fourth fluid manifold.

6. A system for use in administrating therapeutic gas to a patient comprising:
A) a source of therapeutic gas;
B) a first equalization valve;
C) said first equalization valve having an inlet and an outlet and including elements to define a first equalization pressure and a second equalization pressure between the inlet and the outlet of said first equalization valve, with the elements being movable to immediately allow flow of gas through said first equalization valve when pressure at the inlet of said first equalization valve is greater than pressure at the outlet of said first equalization valve plus the first equalization pressure, or the pressure at the outlet of said first equalization valve is greater than pressure at the inlet of said first equalization valve plus the second equalization pressure, and to prevent flow through said first equalization valve at all other pressure conditions;
D) a first fluid manifold having an inlet end fluidically connected to said first equalization valve;
E) a first pressure sensor fluidically connected to said first fluid manifold, the first pressure sensor including a signal generator which generates a signal corresponding to fluid pressure in said first fluid manifold;
F) a first pressure regulator fluidically connected to said first fluid manifold and fluidically connected to a second fluid manifold;
G) a pressure relief valve fluidically connected to said second fluid manifold;
H) a first solenoid controlled valve fluidically connected to said second fluid manifold, said first solenoid controlled valve including a mechanism which controls operation of said first solenoid controlled valve in accordance with signals received;
I) a muffler fluidically connected to said first solenoid controlled valve;
J) a second solenoid controlled valve fluidically connected to said second fluid manifold, said second solenoid controlled valve being controlled in accordance with signals received and being fluidically connected to a third fluid manifold;

K) an outlet end of said first fluid manifold;

L) a fluid reservoir unit having an outlet;

M) a fourth fluid manifold having an inlet end fluidically connected to the outlet of said fluid reservoir unit;

N) a second pressure sensor fluidically connected to said fourth fluid manifold and including a signal generator which generates a signal corresponding to fluid pressure of fluid in said fourth fluid manifold; and O) a second pressure regulator fluidically connected to said fourth fluid manifold.

7. The system defined in claim 6 wherein said fluid reservoir unit includes a portion of coiled tubing.

* * * * *